United States Patent [19]

Forrest et al.

[11] Patent Number: 4,745,073
[45] Date of Patent: May 17, 1988

[54] MANUAL IMMUNOASSAYS AND APPARATUS THEREFOR

[75] Inventors: Gordon Forrest, Ingatestone; John F. Stivala, South Harrow, both of England

[73] Assignee: Serono Diagnostics Ltd., England

[21] Appl. No.: 501,773

[22] Filed: Jun. 7, 1983

[30] Foreign Application Priority Data

Jun. 8, 1982 [GB] United Kingdom ................ 8216595

[51] Int. Cl.$^4$ ................... G01N 33/53; G01N 33/538; G01N 33/553
[52] U.S. Cl. ................... 436/518; 206/204; 215/1 R; 215/1 C; 215/227; 215/228; 422/101; 422/102; 436/524; 436/526; 436/528; 436/531; 436/541; 436/807; 436/810; 436/824
[58] Field of Search .............. 422/101, 102; 215/1 R, 215/1 C, 227, 228; 206/204; 436/518, 524, 526, 528, 531, 541, 807, 810, 824

[56] References Cited

U.S. PATENT DOCUMENTS

| 2,240,101 | 4/1941 | Smith | 422/102 |
| 2,362,796 | 11/1944 | Boesel | 215/227 X |
| 3,079,022 | 2/1963 | Tompkins | 215/227 X |
| 3,449,081 | 6/1969 | Hughes | 422/101 X |
| 4,090,850 | 5/1978 | Chen | 422/102 X |
| 4,180,383 | 12/1979 | Johnson | 422/102 X |
| 4,248,355 | 2/1981 | Kolb | 422/102 X |
| 4,320,087 | 3/1982 | Chau | 422/102 X |
| 4,362,698 | 12/1982 | Boosalis | 422/102 |
| 4,418,702 | 12/1983 | Brown | 422/102 X |
| 4,454,235 | 6/1984 | Johnson | 422/102 X |

FOREIGN PATENT DOCUMENTS 1242466 8/1971 United Kingdom .
1535411 12/1978 United Kingdom .

Primary Examiner—Sidney Marantz
Attorney, Agent, or Firm—Ostrolenk, Faber, Gerb & Soffen

[57] ABSTRACT

A cap for a container in which immunoassays are performed includes a liquid absorbing material accessible to liquid in the container.

10 Claims, 1 Drawing Sheet

MANUAL IMMUNOASSAYS AND APPARATUS THEREFOR

This invention relates to immunoassays, more particularly to immunoassays which involve a phase separation step and which are effected manually.

It is well known that in certain immunoassays conducted on liquid samples, a mixture is formed comprising a liquid and a solid. The solid may, for example, comprise a reagent in insolubilised form, e.g. a reagent bound to an insoluble support, or it may be a product of the reaction, e.g. a precipitate formed after the primary reaction by, for example, addition of a second antibody or polyethylene glycol, or it may be an adsorbent for one component of the liquid, e.g. charcoal adsorbent. The reaction liquid is separated from the solid before completion of the assay. Such assays usually involve the use of a label, e.g. a radioactive atom, and the amount of the substance under assay (normally an antigen, hapten or antibody) is determined by measurement of the amount of label remaining in the liquid or becoming attached to the solid.

In assays of this type which are conducted manually, the solid is usually either finely divided particles or a coating on the wall of the reaction vessel (usually a test tube). The separation step is effected by decanting the liquid phase from the reaction vessel. In order to facilitate this in the case a particulate solid phase, the mixture may be centrifuged (after incubation) to consolidate the particles at the bottom of the vessel. Alternatively, and usually more preferably, particles are used which include magnetically attractable material, so that the particles can be sedimented and retained in the reaction vessel during decantation by the application of a magnetic field.

There are special problems in the use of radioactive labels in that great care has to be taken in the separation step to avoid contamination both of personnel and of the environment by the radioactive material. Thus, the decantation step has to be effected with care and precautions taken to avoid spillage and contamination in other ways. Furthermore, where it is desired to measure the label in the liquid phase, the liquid cannot be poured to waste but must be conserved until after measurement.

We have now devised a way in which many of these problems can be reduced or avoided completely, and whereby both time and labour may be saved in conducting the assay. In accordance with a feature of the invention, we provide a cap for application to the opening of a container to close the container in liquid-tight fashion, wherein the cap includes a liquid-absorbing material which is accessible to liquid in the container so that, when a closed container with liquid therein is inverted, the said material absorbs the liquid. In further aspects, the invention includes a method of immunoassay utilising a container with such a cap, and also a container and cap therefor per se.

In accordance with the invention, the final immunoassay reaction mixture (including a solid phase, usually an insolubilised reagent) is formed in a reaction vessel. The vessel will normally be a small test-tube (as is well known for use in manual immunoassays) although other types of vessel may equally be used. The open end of the test-tube or the vessel opening is then closed with a cap of the invention, the reaction mixture thus being sealed in the test-tube in liquid-tight fashion. After incubation, the phase separation step is effected by inverting the test-tube to bring the liquid phase into contact with the absorbent material in the cap. Effectively, all the liquid is absorbed and held in the material, so that upon handling the test-tube thereafter, only the solid phase remains in the tube itself, the liquid phase being retained in the absorbent material in the cap. In the case of a radioactive label, either the solid phase, or the liquid phase, can then be counted by placing the test-tube in an appropriate counter.

As will be clear to those skilled in the art, it is important to avoid solid phase entering the absorbent material. In practice, this is easily achieved. Where the solid phase is in the form of a coating on the lower part of the wall of the test-tube, there is no problem. When magnetically attractable particles are used as the solid phase, these can be retained in the tube during inversion by use of a magnetic field. Racks for this purpose are known in the art and are described, for example, in Europeaun patent specification No. 30086 to which reference should be made for further details. In the case of non-magnetic particles, it will usually be necessary to centrifuge before inversion, to consolidate the particles (or other solids) at the bottom of the test-tube.

It is an important feature of the invention that, once the cap has been applied to the test-tube or other vessel, the contents are sealed therein and the remainder of the assay and (if the container is disposable) the discarding of the reactants after the assay, can be effected without opening the vessel. This very substantially reduces the risk of contamination and of inadvertent spillage which could affect the accuracy of the assay result. These factors are particularly important when a radioactive label is used.

Whilst the cap can be made of any suitable substance, plastics caps are both cheap and convenient. In the case of caps for test-tubes and the like, the cap may be of cup-shape with adsorbent material lodged therein and exposed to the liquid contents of the tube through the open end of the cap. The cap may be provided with one or more circumferential ribs to bear against the wall of the test-tube to form a liquid tight, push-fit, seal. Whilst push-fit caps are preferred, other arrangements are equally possible (e.g. screw-fit caps etc.).

The absorbent material can be of various kinds, e.g. sponge material with or without chemical absorbents, but is preferably of the cellulose wadding type, such as is commonly used as filter material in smoking articles, e.g. cigarettes and pipes, or for reservoirs in pens. One such filter material is called "Transorb" (trade mark). The amount of absorbent material must be sufficient to absorb all the liquid phase from the reaction vessel. For most purposes, the volume of liquid phase in manual immunoassays will not greatly exceed about 1 ml. and the provision of adequate absorbent material for this purpose in a cap is not a problem. It is preferred to provide in the absorbent material, one or more elongate channels (extending generally parallel to the longitudinal axis of the test-tube or the like) to ensure that the liquid is quickly absorbed by the material.

Where a radiolabel is used in the assay and it is desired to count the solid phase remaining in the vessel after the separation step, the absorbent material may advantageously contain a radioactivity quencher (usually a heavy metal oxide such as bismuth trioxide). This will reduce the chance of any of the radiolabel in the absorbed liquid contributing to the radio-count of the solid phase.

Many manual immunoassays are conducted on a batch basis (see European specification No. 30086), by arranging a series of reaction test-tubes in a rack. By using a cap of the invention on each tube, the whole rack can be inverted (after incubation) to effect the separation step. This procedure can be automated, so that after a given incubation period, the rack is automatically inverted and then, after the liquid in each tube has been absorbed, the rack is returned to its normal position. The tubes can then be subjected to radiolabel counting. This is a particularly advantageous procedure where the solid phase is a coating on the test-tube wall or magnetically attractable particles. In the latter case, means are provided for automatically applying a magnetic field to sediment the particles after incubation but before inversion of the rack.

BRIEF DESCRIPTION OF THE DRAWINGS

In order that the invention may be more fully understood, reference is made to the accompanying drawing, wherein.

Figure 1:
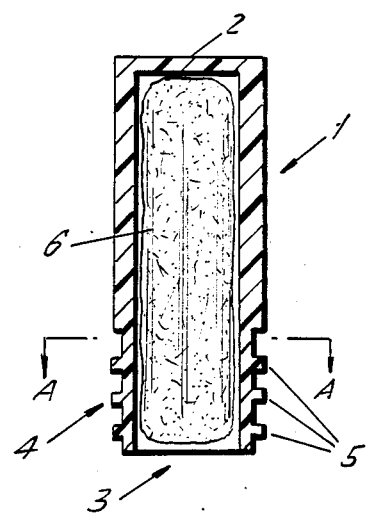
FIG. 1 is a longitudinal sectional view of one embodiment of cap of the invention.
Figure 2:
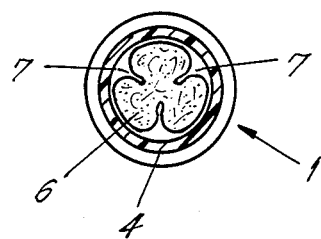
FIG. 2 is a section on the line A—A of FIG. 1.

Referring to the drawings, the cap comprises a plastics moulding 1 in the form of an elongate cup-shape, one end 2 of which is closed and the other end 3 is open. The moulding has a necked portion 4 to be received in the open end of a test-tube (not shown). Circumferential ribs 5 are provided to seal against the internal wall of the test-tube. Elongate cellulose "filter" material 6 is a friction fit within the cap, and (as shown in FIG. 2) includes elongate channels 7 therein to enable the liquid to penetrate the material for absorption thereby.

To assist in keeping the "filter" material 6 within the cap, an annular flange (not shown) may be provided inwardly of the open end 3 of the cap.

We claim:

1. A closure for a small generally tubular container used in immunoassays for containing a liquid under assay consisting essentially of a cap receivable in liquid-tight fashion on said container to close the same and prevent material in said container from exiting said container at any time when closed by said cap, said cap including a liquid-absorbing material accessible to liquid in said container so that, when a closed container with liquid therein is inverted, the liquid absorbing material in the cap absorbs the liquid and retains it therein when the closed container is returned in an upright position thereby separating the absorbed liquid from any solid material in the container.

2. A closure according to claim 1 which is a hollow plastics body having said liquid-absorbing material located therein.

3. A closure according to claim 1 or 2, wherein the liquid-absorbing material is a cellulose wadding or a sponge material.

4. A closure according to claim 1 or 2, wherein the said liquid-absorbing material contains a radioactive quencher.

5. A closure according to claim 1 or 2, wherein the liquid-absorbing material has at least one elongate channel therein to facilitate absorption of liquid.

6. In combination, a small generally tubular container for use in immunoassays for containing a liquid under assay, and a closure therefor, which closure is receivable on the open end of the container in liquid-tight fashion, the closure being as defined in claim 1.

7. The combination according to claim 6, in which the container is in the general form of a test-tube, and wherein the closure is adapted to be pushed-fit in the open end of the test-tube.

8. The combination according to claim 6 or 7, in which the container has a reagent coating on the inner wall thereof.

9. A method of immunoassay in which a reaction mixture is formed comprising a liquid phase and a solid phase, and wherein the solid phase is separated from the liquid phase, characterized in that there is used a combination of a small generally tubular container for use in immunoassays for containing a liquid under assay and a closure therefore, which closure is receivable on the open end of the container in liquid-tight fashion, the closure consisting essentially of a cap receivable in liquid-tight fashion on said container to close the same and prevent material in said container from exiting said container at any time when closed by said cap, said cap including a liquid-absorbing material accessible to liquid in said container so that, when a closed container with liquid therein is inverted, the liquid absorbing material in the cap absorbs the liquid and retains it therein when the closed container is returned in an upright position thereby separating the absorbed liquid from any solid material in the container, and wherein the said separation is effected by inverting the closed container whereby the liquid is absorbed by the liquid-absorbing material in the cap, the solid phase being retained in the container.

10. The method according to claim 9 in which the container is in the general form of a test-tube, and wherein the closure is adapted to be pushed-fit in the open end of the test-tube.

* * * * *